US008522630B1

(12) United States Patent  
Mayeaux

(10) Patent No.: US 8,522,630 B1
(45) Date of Patent: Sep. 3, 2013

(54) SYSTEM FOR RETRIEVING A FLUID SAMPLE FROM A FLUID SAMPLE SOURCE

(75) Inventor: Donald P. Mayeaux, Prairieville, LA (US)

(73) Assignee: A+ Manufacturing, LLC, Gonzales, LA (US)

( * ) Notice: Subject to any disclaimer, the term of this patent is extended or adjusted under 35 U.S.C. 154(b) by 385 days.

(21) Appl. No.: 12/822,920

(22) Filed: Jun. 24, 2010

Related U.S. Application Data

(60) Provisional application No. 61/288,317, filed on Dec. 20, 2009.

(51) Int. Cl.
*G01D 21/00* (2006.01)
*G01N 17/00* (2006.01)
*G01N 1/16* (2006.01)
*G01N 1/00* (2006.01)

(52) U.S. Cl.
USPC ......... 73/866.5; 73/86; 73/863.82; 73/863.86

(58) Field of Classification Search
USPC ........... 73/866.5, 86, 863.81, 863.82, 863.85, 73/863.86; 422/53
See application file for complete search history.

(56) References Cited

U.S. PATENT DOCUMENTS

| 3,174,332 | A | * | 3/1965 | Echtler, Jr. et al. | 73/86 |
| 4,327,586 | A | * | 5/1982 | Goddard | 73/866.5 |
| 5,106,580 | A | | 4/1992 | Mudiam | |
| 5,551,707 | A | * | 9/1996 | Pauley et al. | 277/654 |
| 6,701,794 | B2 | | 3/2004 | Mayeaux | |
| 6,827,486 | B2 | | 12/2004 | Welker | |
| 6,964,517 | B2 | | 11/2005 | Welker | |
| 7,472,615 | B2 | | 1/2009 | Mayeaux | |
| 2005/0072253 | A1 | * | 4/2005 | Scott et al. | 73/866.5 |
| 2005/0223829 | A1 | * | 10/2005 | Mayeaux | 73/866.5 |
| 2005/0247108 | A1 | * | 11/2005 | Mayeaux | 73/29.01 |

* cited by examiner

*Primary Examiner* — Hezron E Williams
*Assistant Examiner* — Nathaniel Kolb
(74) *Attorney, Agent, or Firm* — Joseph T Regard, Ltd plc

(57) ABSTRACT

A system for retrieving a fluid sample from a fluid source. The preferred embodiment of the present invention contemplates a system for insertion of a probe into a pressurized fluid stream by means of male threads which are threadly engaged in a female threaded housing. An elastomeric seal is employed to form a fluid barrier around a segment of the probe's outer surface.

27 Claims, 7 Drawing Sheets

US 8,522,630 B1

SYSTEM FOR RETRIEVING A FLUID SAMPLE FROM A FLUID SAMPLE SOURCE

BENEFIT CLAIM

The present application claims the benefit of U.S. Provisional Patent Application Ser. No. 61/288,317 filed Dec. 20, 2009, entitled "System for Retrieving a Fluid Sample from a Fluid Sample Source", listing Donald P. Mayeaux as inventor.

FIELD OF THE INVENTION

The present invention relates to sampling systems, and in particular to a system for retrieving a fluid sample from a fluid source. The preferred embodiment of the present invention contemplates a system for insertion of a probe into a pressurized fluid stream by means of male threads which are threadly engaged in a female threaded housing. An elastomeric seal is employed to form a fluid barrier around a segment of the probe's outer surface.

BACKGROUND OF INVENTION

It is common practice for fluid samples to be extracted from a pressurized pipeline for "on-line" analysis or laboratory analysis. Such is the case in the natural gas industry wherein the monetary value of the gas is dependent on its composition. The chemical and oil refining industries also have needs for extracting fluid samples from pressurized fluid sources.

Additionally sensors, such as pressure and temperature sensors and corrosion coupons often require insertion into pressurized fluid streams. There are many probe types designed to be inserted into pressurized fluid systems. There are pressure balance insertion methods, such as described in Mayeaux U.S. Pat. Nos. 7,472,615 and 6,701,794, which do not require forcing the probe through a seal. There are smooth walled probe types, such as described in Welker U.S. Pat. Nos. 6,964,517 and 6,827,486, which are forced through a seal into a pressurized fluid by pneumatic or hydraulic means. Another probe insertion method utilizes a threaded male membrane and threaded female nut to force a smooth walled probe through a seal into the pressurized fluid. An example is the Mudiam U.S. Pat. No. 5,106,580.

The aforementioned methods of probe insertion each have drawbacks. For example, the Mayeaux patents require a housing with foot valve which prevents it from being utilized in a horizontal position. The Welker patents describe probes requiring valving and pneumatic or hydraulic cylinders which complicates their construction and operation. The Mudiam patent describes a complex apparatus in which a rod type of probe is inserted by utilizing a separate threaded member.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein.

DETAILED DISCUSSION OF THE INVENTION

The present invention is a simple device in which the probe has external threads which, when rotated, inserts itself into a pressurized fluid source through a threaded seal and a threaded female member. The probe may be configured to extract a fluid sample, insert a sensor or corrosion coupon, or perform a variety of tasks requiring insertion into a pressurized fluid.

Unlike prior art which utilizes a threaded member to force a smooth walled rod or probe into a pressurized fluid container through a seal, the current invention utilizes a seal around the threaded area of the threaded member. This significantly simplifies the construction and reduces the risk of the probe blowing out of the seal.

Figure 1:
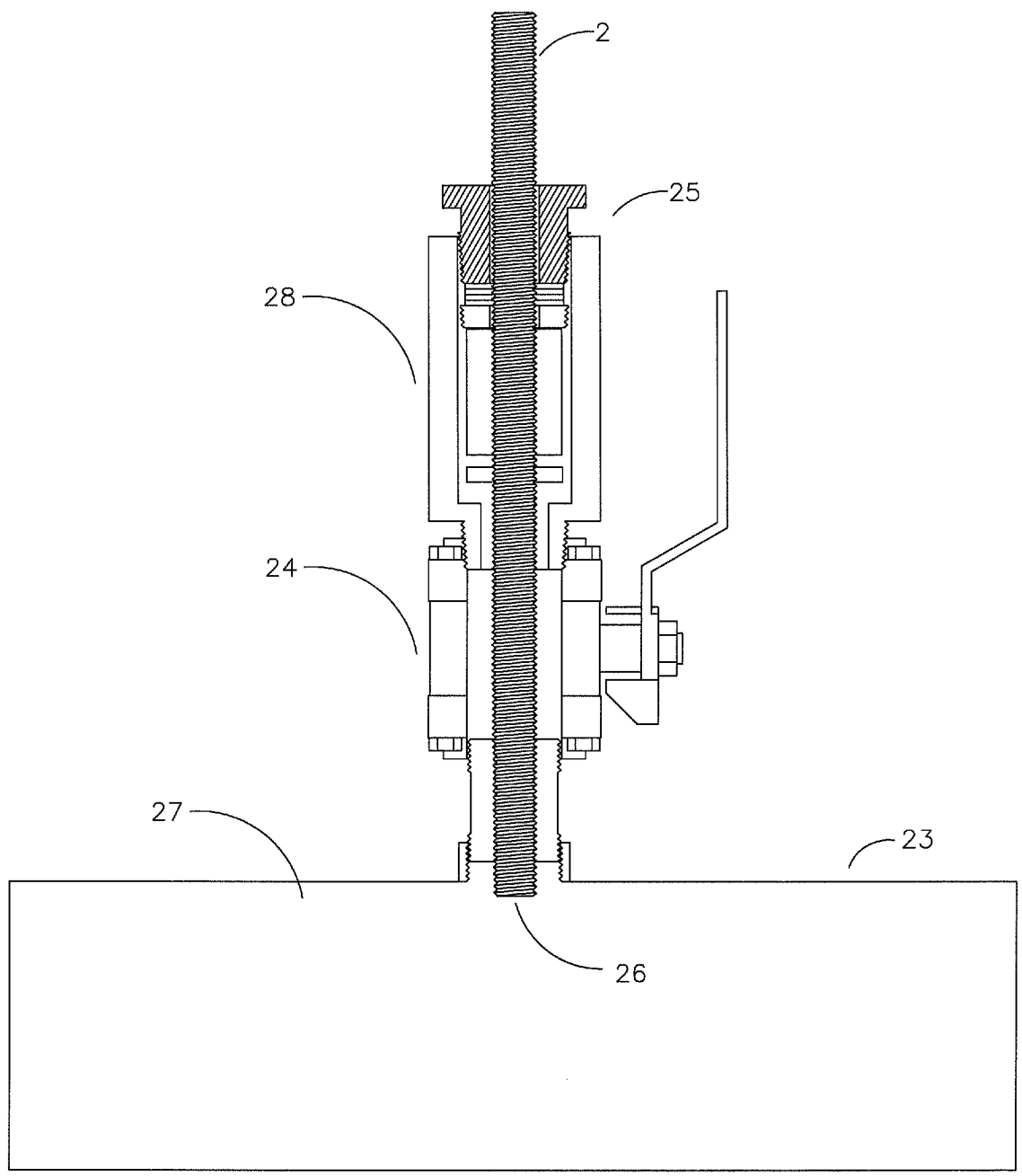
FIG. 1 is a side, partially cut-away view of a preferred embodiment of the insertion assembly of the present invention mounted to a pipeline through an open valve, with a probe tip situated in pressurized fluid.

In the preferred embodiment of the present invention, refer to FIG. 1, insertion assembly 25 is mounted to a pipeline 23 through full opening valve 24 wherein probe tip 26 is located in a pressurized fluid 27.

Figure 2:
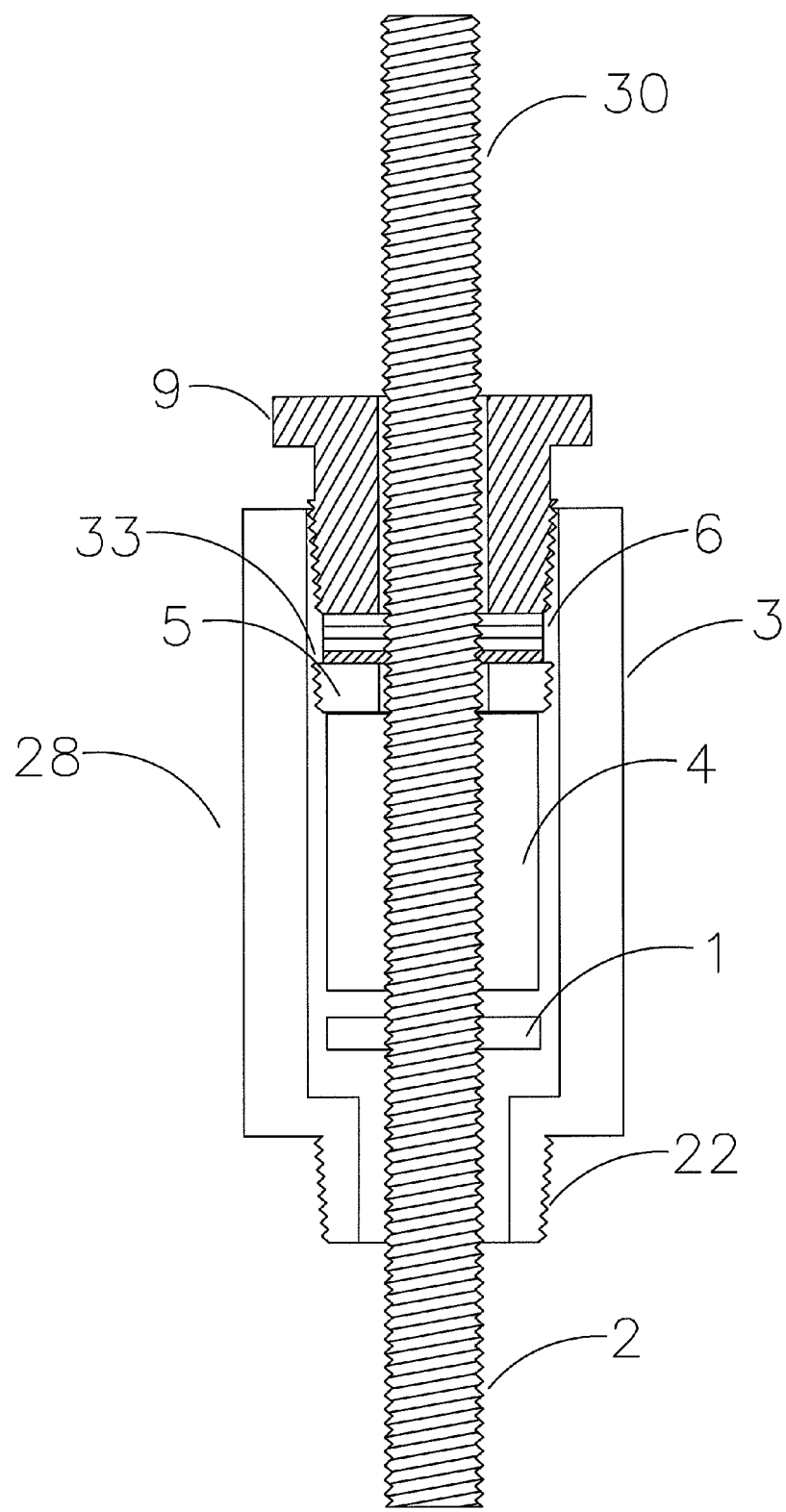
FIG. 2 is a side, partially cut-away view of the invention of FIG. 1, illustrating a closer view of the packing gland, female thread insert, retention nut, and related components.

Housing assembly 28, refer to FIG. 2, consists of housing 3, having an NPT threaded end 22, a thread die or threaded nut 1, female threaded insert 4, insert retention nut 5, packing gland 6, packing gland retention nut 9, and threaded probe shaft 2, having male threads 30.

When insertion assembly 25 is mounted to a pressurized fluid source 27 as shown in FIG. 1 rotating threaded probe shaft 2 (for example, via handle, lever or actuator associated with the probe shaft) will result in said probe shaft 2 being raised or lowered depending on the direction of rotation and thread direction. Female thread insert 4, locked in place by insert retention nut 5, provides the female thread engagement necessary to raise and lower said probe shaft 2 when said probe shaft 2 is rotated.

Figure 7:
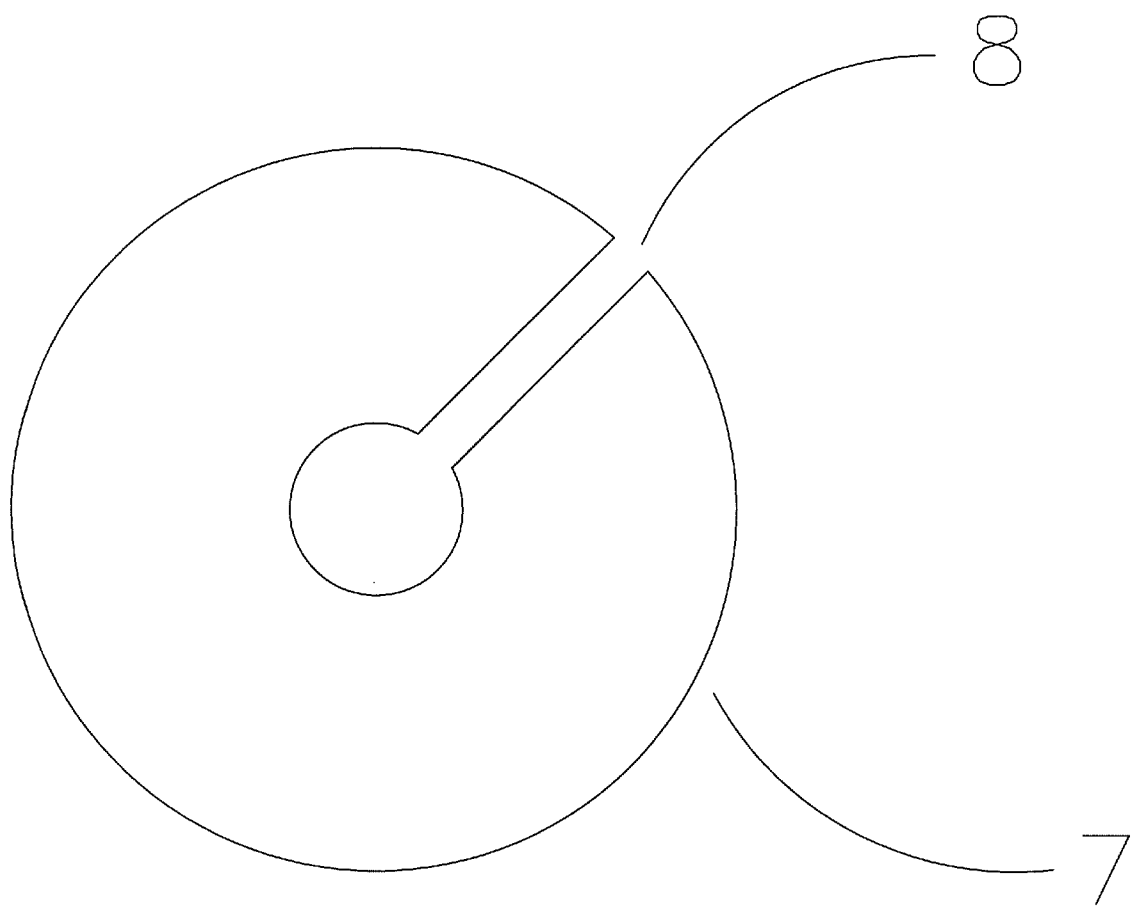
FIG. 7 is a top view illustrating a split disc used to form the packing gland 6 of FIG. 2.

Packing gland 6 is compressed and made to flow tightly around male threads 30 of threaded probe shaft 2 by rotating packing gland retention nut 9. Packing gland 6 as shown in FIG. 2 is constructed of a plurality of single elastomeric split disc 7 which may be slit 8 (Refer to FIG. 7) to accommodate placement around threaded probe shaft 2 after insertion assembly 25 is fully assembled. Refer to FIG. 7. Packing gland 6 may also contain a layer 33, said layer 33 being impervious to a process fluid thereby providing protection against attack of process fluids upon packing gland 6. Packing gland retention nut 9 can be rotated to maintain a leak free fluid seal while insertion assembly 25 is in service.

The primary purpose of thread die or threaded nut 1 is to remove scale from the threads as the probe is retracted should said scale accumulate while the probe is exposed to a process fluid. Female thread insert 4 is preferably constructed of a plastic material such as Kevlar. Said plastic threads provides for smooth, low torque rotation of probe shaft 2, said probe shaft 2 is preferably construction of stainless steel. Threaded die or threaded nut 1 also provides a measure of protection against ejection of probe shaft 2 in the event that housing assembly 28 is installed in a pressurized fluid system having a fluid pressure substantially higher than the pressure rating of said housing assembly 28 resulting in the stripping of threads in female threaded insert 4.

Figure 3:
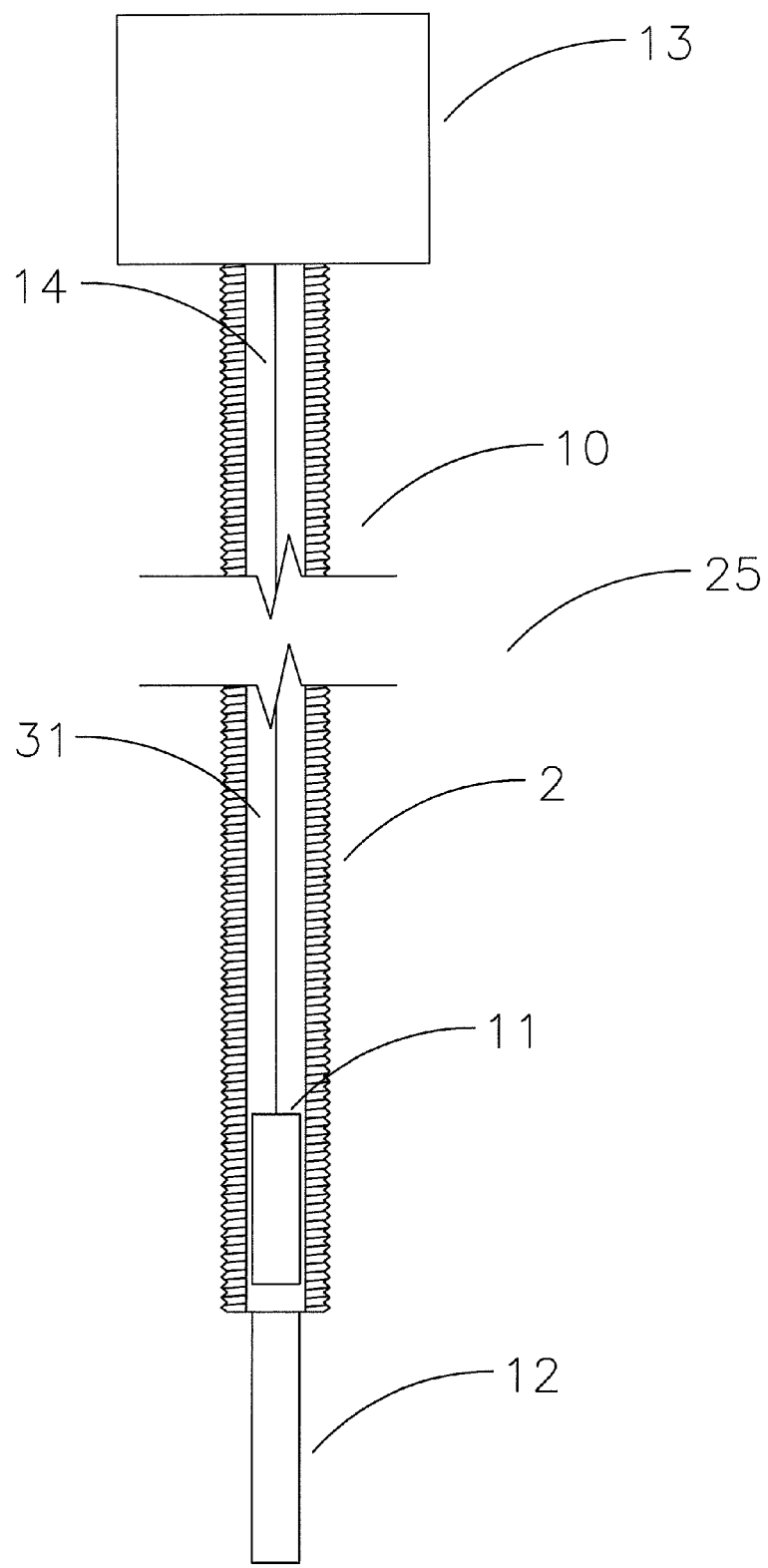
FIG. 3 is a side, partially cross-sectional view of the threaded shaft of FIG. 1, illustrating regulator mounted thereon to its first end, a with pressure regulator mounted situated within said threaded shaft adjacent to its second end, a force transfer rod situated therebetween, and a membrane probe top in communication with said pressure regulator valve cartridge, said probe tip emanating from said second end of said threaded shaft.
Figure 4:
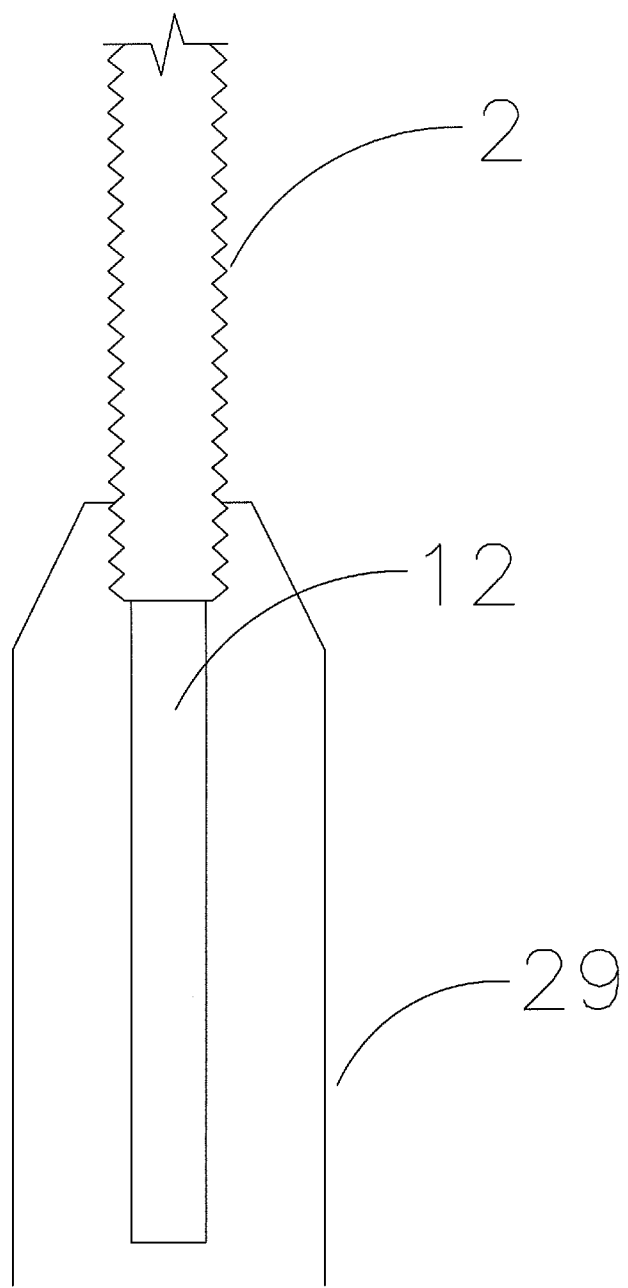
FIG. 4 is a side, cut-away view of the probe tip of FIG. 3, with a shroud situated thereabout.

Insertion assembly 25 can be utilized to perform a fluid sample extraction task when threaded probe shaft 2 is configured as shown in FIG. 3. A passage 31 provides fluid communication between regulator body 13 and pressure regulator valve cartridge 11, said passage 31 also houses force transfer rod 14 which provides mechanical communication between a pressure regulating diaphragm (not shown) located in regulator body 13 and the pressure regulator valve cartridge 11. In the preferred embodiment a phase separation membrane tip 12 filters solids and entrained liquids when the fluid to be sample is a gas. In operation, gas filtered of solids and liquid by phase separation member tip 12, flows into pressure regulator valve cartridge wherein the pressure is regulated, said gas then flows into passage 31, around force transfer rod 14, to regulator body 13 wherein it exits from a port which is not shown. In a similar manner, threaded probe shaft 2 can be configured to extract a fluid sample without pressure regulation or membrane filtration. In cases wherein threaded probe shaft 2 is configured with a phase separation membrane tip a shroud 29, refer to FIG. 4, may be positioned around phase separation membrane tip 12 to protect said phase separation membrane tip 12 from damage from high fluid flow or entrained solids.

Figure 5:
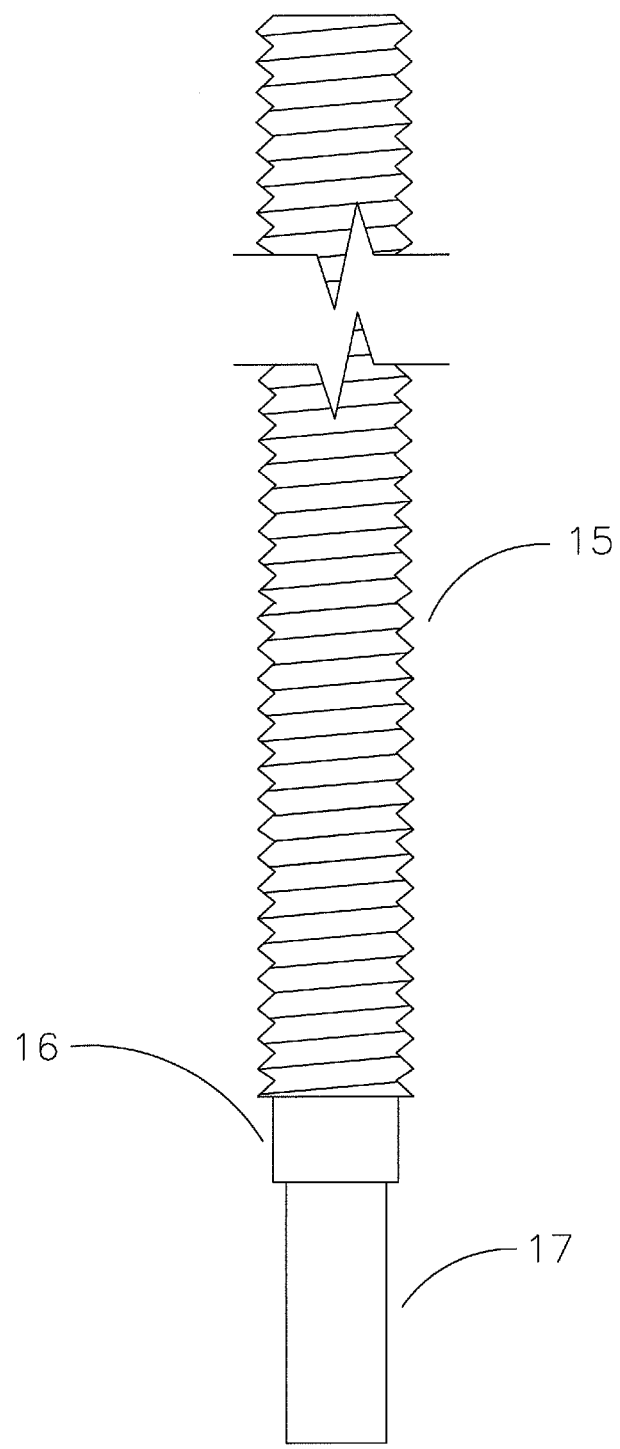
FIG. 5 is a side, close-up view of the probe tip of FIG. 1, but with a corrosion coupon mounted thereon.

In a second embodiment of the present invention threaded probe shaft 15 is configured to receive a corrosion coupon, refer to FIG. 5. In said second embodiment corrosion coupon adapter 16 provides a transition between probe adapted for insertion of corrosion coupon 15 and corrosion coupon 17. Said threaded probe shaft 15 adapted for insertion of corrosion coupon 17 does not require a fluid passage.

Figure 6:
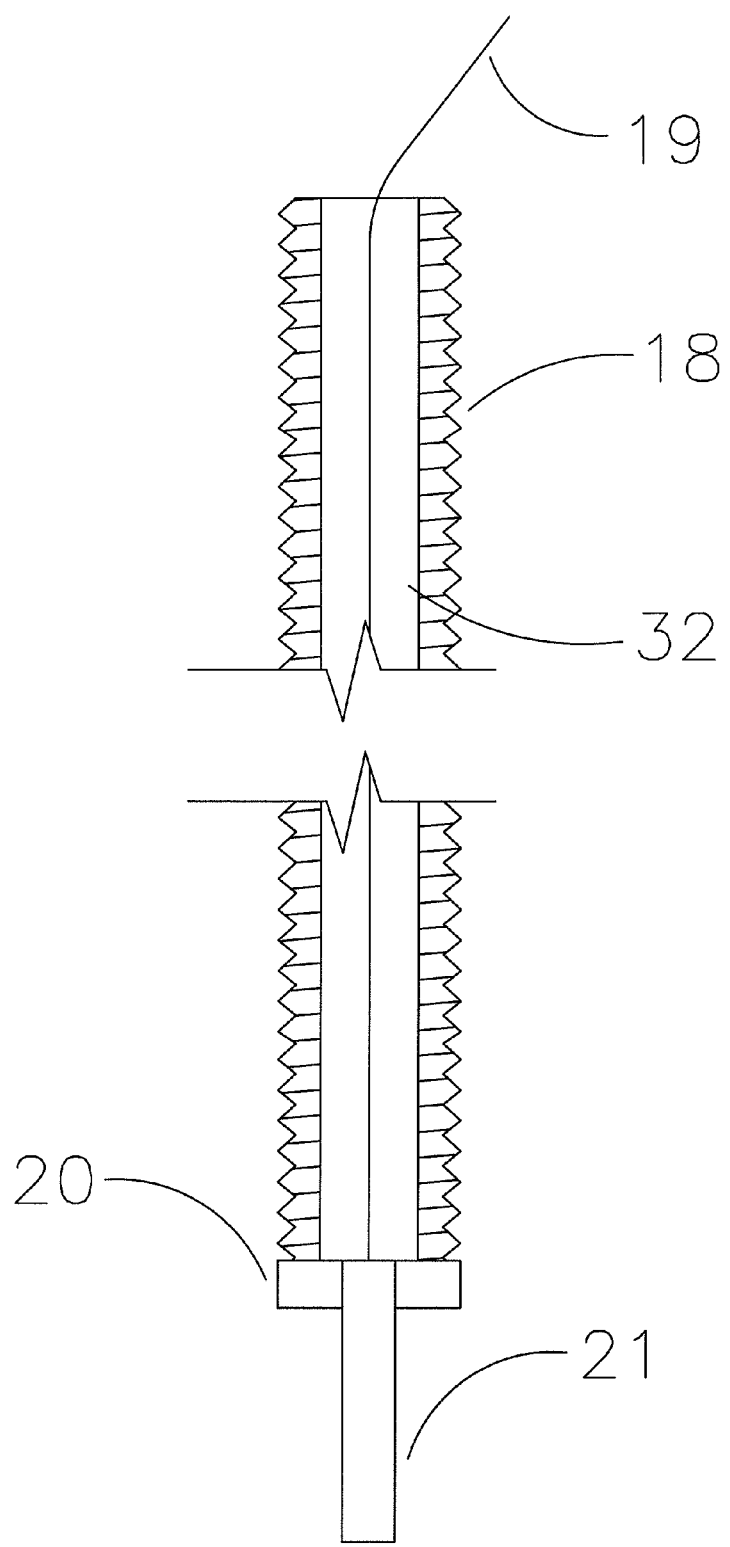
FIG. 6 is a side, close-up view of the probe tip of FIG. 1, but with a sensor mounted thereon, with a sensor cable running through the treaded probe shaft.

In a third embodiment of the present invention threaded probe shaft 18 is configured for mounting and insertion of sensors 21, refer to FIG. 6. In said third embodiment said probe shaft 18 has a passage 32 which houses sensor cable 19. Pressure seal 20 provides a fluid barrier between a pressurized fluid into which sensor 21 has been inserted and passage 32.

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

What is claimed is:

1. An insertion assembly comprising:
    a housing having a passage formed therethrough having first and second ends, said first end of said passage formed to fluidly engage a pressurized fluid source;
    a first retention nut having a probe shaft passage formed therethrough, said first retention nut having an outer diameter formed to threadingly engage said inner diameter of said housing passage in the vicinity of second end of said housing passage;
    a second retention nut having a probe shaft passage formed therethrough, said second retention nut having an outer diameter formed to threadingly engage the said inner diameter of said housing passage;
    a packing gland situated between said first and second retention nuts;
    a threaded shaft having first and second ends, an outer diameter, and a length having a fluid passage formed therethrough, said threaded shaft extending through said probe shaft passages of said first and second retention nuts and through said first and second ends of said housing passage, said threaded shaft forming a probe shaft;
    wherein said packing gland forms a fluid barrier about said outer diameter of said threaded shaft so as to prevent the escape of pressure from said pressurized fluid source.

2. The invention of claim 1 wherein said first end of said housing has NPT pipe threads formed at said first end of said passage.

3. The invention of claim 1 wherein said first end of said housing is formed for flanged mounting.

4. The invention of claim 1 wherein said packing gland is formed of layered, elastomeric split discs.

5. The invention of claim 1 wherein said packing gland is constructed from elastomeric material.

6. The invention of claim 5 wherein said packing gland is constructed from a plurality of layers.

7. The invention of claim 6 wherein the layer of said packing gland exposed to the process is impervious to said fluid in said pressurized fluid source.

8. The invention of claim 7 wherein said packing gland is formed to be adjustably compressable by adjusting said first or second retention nuts so as to provide a leak proof fluid barrier under varying conditions.

9. The invention of claim 1 wherein the said threaded shaft has a fluid passage through its axis.

10. The invention of claim 9 wherein said fluid passage is formed to facilitate the flow therethrough of a fluid sample from a pressurized fluid source.

11. The invention of claim 10 wherein said threaded shaft fluid passage has situated therein a pressure regulator valve cartridge in the vicinity of said first end of said threaded shaft, said second end of said threaded shaft has a regulator body associated therewith, and a force transfer rod engaging said pressure regulator valve cartridge with said regulator body, so as to provide mechanical communication between said regulator body and said pressure regulator valve cartridge to facilitate integral pressure control.

12. The invention of claim 10 wherein said fluid sample is filtered.

13. The invention of claim 12 wherein said filtration is by use of a phase separation membrane.

14. The invention of claim 1 wherein said threaded shaft is formed to facilitate the passage of objects therethrough to engage a pressurized fluid.

15. The invention of claim 14 wherein said object is comprises a corrosion coupon.

16. The invention of claim 14 wherein said object is comprises a sensor.

17. The invention of claim 16 wherein said sensor comprises a pressure sensor.

18. The invention of claim 16 wherein said sensor comprises a temperature sensor.

19. The invention of claim 14 wherein said object comprises a composition analyzer.

20. The invention of claim 14 wherein said object comprises a composition monitor.

21. The invention of claim 1 wherein there is further provided an insert in said housing passage between said second retention nut and said first end of said housing, said insert having formed therethrough a threaded passage in threaded engagement with said threaded shaft.

22. The invention of claim 21 wherein said second retention nut is formed to lock said insert in place, so that said insert threadingly engages said threaded rod to facilitate the repositioning of said threaded shaft through said housing by the axial rotation of said threaded shaft.

23. The invention of claim 22 wherein said insert is constructed from a plastic material.

24. The invention of claim 23 wherein said plastic material is Kevlar.

25. The invention of claim 1 wherein said insertion assembly is also comprised of a cleaning die or threaded nut threadingly engaging said threaded rod between said insert and said first end of said housing.

26. The invention of claim 25 wherein said cleaning die or nut is adapted for restraining said threaded shaft in the event of thread failure.

27. The invention of claim 1 wherein there is further provided a valve situated between said first end of said housing and said fluid source container, said valve configured to selectively open to allow said first end of said threaded shaft to pass from said housing, through said open valve and into said pressurized fluid source container.

* * * * *